US00PP25101P2

(12) United States Plant Patent
Misato

(10) Patent No.: US PP25,101 P2
(45) Date of Patent: Nov. 25, 2014

(54) ***MANDEVILLA* PLANT NAMED 'SUNPARAREKIN'**

(50) Latin Name: *Mandevilla hybrida*
Varietal Denomination: Sunpararekin

(71) Applicant: Tomoya Misato, Shiga (JP)

(72) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 75 days.

(21) Appl. No.: 13/815,166

(22) Filed: Feb. 5, 2013

(51) Int. Cl.
*A01H 5/00* (2006.01)

(52) U.S. Cl.
USPC ..... Plt./232

(58) Field of Classification Search
CPC ..... A01G 17/02; A01H 5/02
USPC ..... Plt./232
See application file for complete search history.

*Primary Examiner* — Wendy C Haas
(74) *Attorney, Agent, or Firm* — C. A. Whealy

(57) ABSTRACT

A new and distinct cultivar of *Mandevilla* plant named 'Sunpararekin', characterized by its upright and vining plant habit; vigorous growth habit; freely branching habit, dense and bushy plant form; dark green-colored leaves; freely flowering habit; long flowering period; and large bright red-colored flowers.

1 Drawing Sheet

Botanical designation: *Mandevilla hybrida.*
Cultivar denomination: 'SUNPARAREKIN'.

CROSS REFERENCE TO CLOSE-RELATED APPLICATIONS

Title: *Mandevilla* Plant Named 'Sunparasupre' (U.S. Plant patent application Ser. No. 13/815,167)

BACKGROUND OF THE INVENTION

The present invention relates to a new and distinct cultivar of *Mandevilla* plant, botanically known as *Mandevilla hybrida* and hereinafter referred to by the name 'Sunpararekin'.

The new *Mandevilla* plant is a product of a planned breeding program conducted by the Inventor in Higashiomi, Shiga, Japan. The objective of the breeding program is to create new freely-branching and vining *Mandevilla* plants with numerous large attractive flowers.

The new *Mandevilla* plant originated from a cross-pollination in Higashiomi, Shiga, Japan in April, 2006 of a proprietary selection of *Mandevilla hybrida* identified as code number 02M5-1, not patented, as the female, or seed parent with a proprietary selection of *Mandevilla hybrida* identified as code number MH51, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2007.

Asexual reproduction of the new *Mandevilla* plant by cuttings in Higashiomi, Shiga, Japan since October, 2007 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'Sunpararekin'. These characteristics in combination distinguish 'Sunpararekin' as a new and distinct *Mandevilla* plant:

1. Upright and vining plant habit.
2. Vigorous growth habit.
3. Freely branching habit, dense and bushy plant form.
4. Dark green-colored leaves.
5. Freely flowering habit.
6. Long flowering period.
7. Large bright red-colored flowers.

Plants of the new *Mandevilla* can be compared to plants of the female parent selection. Plants of the new *Mandevilla* differ primarily from plants of the female parent selection in the following characteristics:

1. Flower petals of plants of the new *Mandevilla* are imbricate whereas flower petals of plants of the female parent selection are not imbricate.
2. Plants of the new *Mandevilla* and the female parent selection differ in flower color as plants of the female parent have lighter red-colored flowers.

Plants of the new *Mandevilla* can be compared to plants of the male parent selection. Plants of the new *Mandevilla* differ primarily from plants of the male parent selection in the following characteristics:

1. Leaves of plants of the new *Mandevilla* are smooth whereas leaves of plants of the male parent selection are coarse in texture.
2. Plants of the new *Mandevilla* and the male parent selection differ in flower color as plants of the male parent selection have deep red purple-colored flowers.

Plants of the new *Mandevilla* can be compared to plants of *Mandevilla hybrida* 'Sunparasupre', disclosed in U.S. Plant patent application Ser. No. 13/815,167. Plants of the new *Mandevilla* and 'Sunparasupre' differ primarily in growth habit as plants of the new *Mandevilla* have shorter lateral branches with longer internodes than plants of 'Sunparasupre'. In addition, plants of the new *Mandevilla* have larger flowers than plants of 'Sunparasupre'.

Plants of the new *Mandevilla* can be compared to plants of the *Mandevilla* 'Sunparakama', disclosed in U.S. Plant Pat. No. 22,366. In side-by-side comparisons conducted in Higashiomi, Shiga, Japan, plants of the new *Mandevilla* differed from plants of 'Sunparakama' in the following characteristics:

1. Plants of the new *Mandevilla* had oblong-shaped leaves whereas plants of 'Sunparakama' had elliptic-shaped leaves.
2. Plants of the new *Mandevilla* had broader flower petals than plants of 'Sunparakama'.
3. Plants of the new *Mandevilla* had wider flower throats than plants of 'Sunparakama'.
4. Plants of the new *Mandevilla* and 'Sunparakama' differed slightly in flower color.
5. Plants of the new *Mandevilla* had longer peduncles than plants of 'Sunparakama'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpararekin' grown in a container.

The photograph at the bottom of the sheet is a close-up view of a typical flowering plant of 'Sunpararekin'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpararekin'.

Parentage:

*Female, or seed, parent*.—Proprietary selection of *Mandevilla hybrida* identified as code number 02M5-1, not patented.

*Male, or pollen, parent*.—Proprietary selection of *Mandevilla hybrida* identified as code number MH51, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Upright and vining plant habit; vigorous growth habit; freely branching habit.

*Lateral branch description*.—Length: About 136.3 cm. Diameter: About 4.7 mm. Internode length: About 8.7 cm. Strength: Strong. Texture: Sparsely pubescent; developed, woody. Color: Close to 146C tinted with close to 177B; developed, close to N199B.

Foliage description:

*Arrangement*.—Opposite, simple.

*Length*.—About 11.5 cm.

*Width*.—About 4.6 cm.

*Shape*.—Oblong.

*Apex*.—Acuminate.

*Base*.—Cordate.

*Margin*.—Entire.

*Texture, upper and lower surfaces*.—Pubescent.

*Venation pattern*.—Pinnate, reticulate.

*Color*.—Developing leaves, upper surface: Close to 144A. Developing leaves, lower surface: Close to 138A. Fully expanded leaves, upper surface: Close to N137C; venation, close to 138B. Fully expanded leaves, lower surface: Close to 138B; venation, close to 138D.

*Petiole length*.—About 1.2 cm.

*Petiole diameter*.—About 2.3 mm.

*Petiole texture, upper and lower surfaces*.—Sparsely pubescent.

*Petiole color, upper and lower surfaces*.—Close to 138A.

Flower description:

*Flower type and habit*.—Single salverform flowers arranged in axillary racemes; flowers face upright to outwardly; freely flowering habit with about three to six flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—Slightly fragrant, pleasant.

*Inflorescence height*.—About 14.8 cm.

*Inflorescence diameter*.—About 13.7 cm.

*Flowers*.—Appearance: Salverform; flared trumpet, corolla fused and five-parted; flowers roughly star-shaped. Diameter: About 10.3 cm. Depth (length): About 7.7 cm. Throat diameter: About 2.4 cm. Tube length: About 5 cm. Tube diameter, mid-section: About 1.7 cm. Tube diameter, base: About 4.5 mm.

*Flower buds*.—Height: About 7.2 cm. Diameter: About 1.6 cm. Shape: Lenticular. Color: Close to 53B.

*Corolla*.—Quantity and arrangement: Five petals arranged in a single whorl and fused towards the base into an elongated tube; petals imbricate. Petal lobe length: About 4.6 cm. Petal lobe width: About 4.9 cm. Petal lobe shape: Orbicular. Petal lobe apex: Mostly obtuse. Petal lobe margin: Entire, undulate. Petal lobe texture, upper and lower surfaces: Smooth, glabrous; velvety. Throat texture: Smooth, glabrous; velvety. Tube texture: Smooth, glabrous; velvety. Color: Petal lobe, when opening, upper surface: Close to 45B. Petal lobe, when opening, lower surface: Close to 47C. Petal lobe, fully opened, upper surface: Close to 46B. Petal lobe, fully opened, lower surface: Close to 53C. Throat: Towards the petal, close to 46A; mid-section and towards the base, close to N25A. Tube: Mid-section and towards the apex, close to 144D; towards the base, close to 53D.

*Calyx*.—Quantity and arrangement: Five sepals arranged in a single whorl; calyx, star-shaped. Sepal length: About 5.7 mm. Sepal width: About 2.9 mm. Sepal shape: Deltoid. Sepal apex: Acute. Sepal base: Truncate. Sepal margin: Entire. Sepal texture, upper and lower surfaces: Smooth, glabrous. Sepal color: When developing, upper and lower surfaces: Close to 145B; apex tinted with close to 58A. Fully developed, upper and lower surfaces: Close to 145B; apex tinted with close to 58A.

*Peduncles*.—Length: About 7.1 cm. Diameter: About 2.7 mm. Texture: Smooth, glabrous. Aspect: Obliquely upright. Color: Close to 137C.

*Pedicels*.—Length: About 1.4 cm. Diameter: About 2.6 mm. Texture: Smooth, glabrous. Aspect: Obliquely upright. Color: Close to 144A tinted with close to 58A.

*Reproductive organs*.—Stamens: Quantity and arrangement: Typically five; filaments fused to corolla; anthers, connivent. Anther shape: Ellipsoidal. Anther size: About 1.5 mm by 8 mm. Anther color: Close to 4B. Pollen amount: Moderate. Pollen color: Close to 4D. Pistils: Quantity: Typically one. Pistil length: About 2.2 cm. Style color: Close to 145D. Stigma shape: Conical. Stigma color: Close to 145B. Ovary color: Close to 145B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpararekin' as illustrated and described.

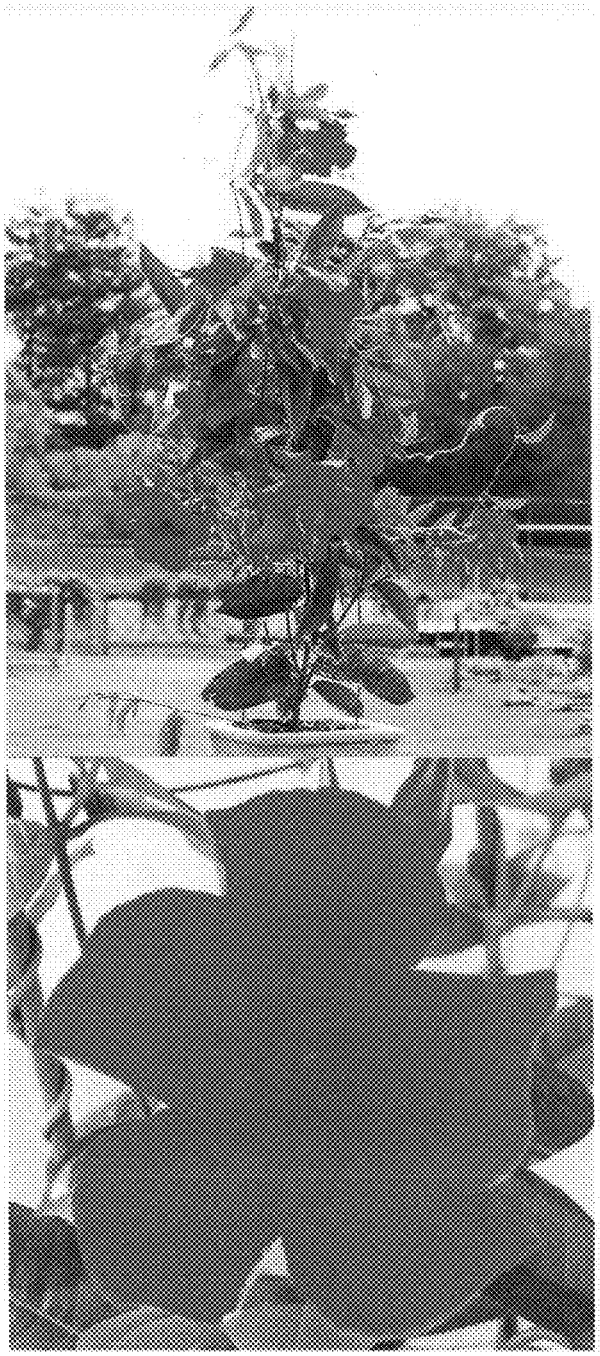

* * * * *